United States Patent [19]

Neal

[11] Patent Number: 4,886,053

[45] Date of Patent: Dec. 12, 1989

[54] STAY FOR ORTHOPEDIC APPLIANCE FOR THE KNEE

[75] Inventor: Charles O. Neal, Knoxville, Tenn.

[73] Assignee: DeRoyal Industries, Inc., Knoxville, Tenn.

[21] Appl. No.: 222,146

[22] Filed: Jul. 21, 1988

[51] Int. Cl.[4] .............................................. A61F 5/01
[52] U.S. Cl. ................................. 128/80 C; 128/87 R; 128/89 R
[58] Field of Search ...................... 128/85, 87 A, 87 R, 128/89 R, 80 R, 80 A–80 H, 165, 166

[56] References Cited

U.S. PATENT DOCUMENTS

| 1,313,344 | 8/1919 | Smart | 128/87 |
|---|---|---|---|
| 2,172,484 | 9/1939 | Tessier | 128/87 |
| 2,318,864 | 5/1943 | Jackson | 128/87 |
| 2,395,468 | 2/1946 | Eames | 144/309 |
| 3,070,091 | 12/1962 | Barnard | 128/89 |
| 3,473,527 | 10/1969 | Spiro | 128/80 R |
| 3,804,084 | 4/1974 | Lehman | 128/80 C |
| 3,934,583 | 1/1976 | Hollingshead et al. | 128/80 C X |
| 4,090,508 | 5/1978 | Gaylord, Jr. | 128/80 C |
| 4,130,115 | 12/1978 | Taylor | 128/80 C |
| 4,423,720 | 1/1984 | Meier et al. | 128/80 C |
| 4,495,942 | 1/1985 | Palumbo | 128/80 H |
| 4,590,932 | 5/1986 | Wilkerson | 128/80 H X |

FOREIGN PATENT DOCUMENTS 1571278  5/1969  France ............... 128/87 R

Primary Examiner—Robert A. Hafer
Assistant Examiner—Kevin G. Rooney
Attorney, Agent, or Firm—Luedeka, Hodges & Neely

[57] ABSTRACT

An improved stay for an orthopedic appliance for the knee which is "self-conforming" to the leg and which provides protection against damage to the peroneal nerve, such stay including a generally planar first section and a bifurcated second section whose legs are disposed on opposite sides of a portion of the peroneal nerve below the fibular head.

6 Claims, 1 Drawing Sheet

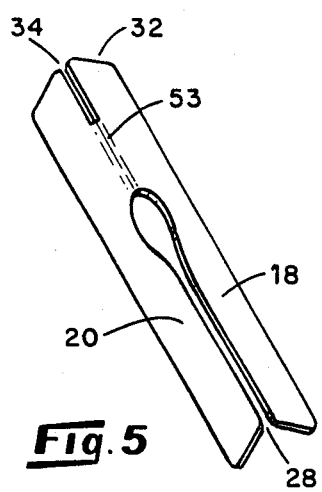
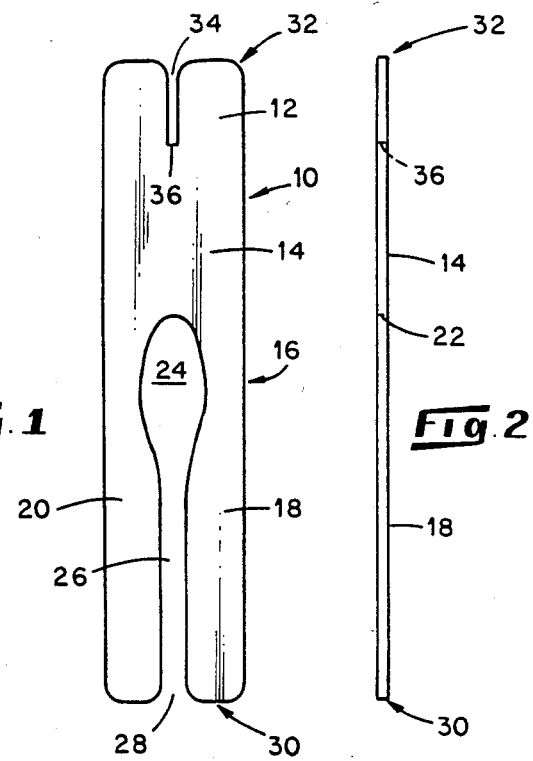
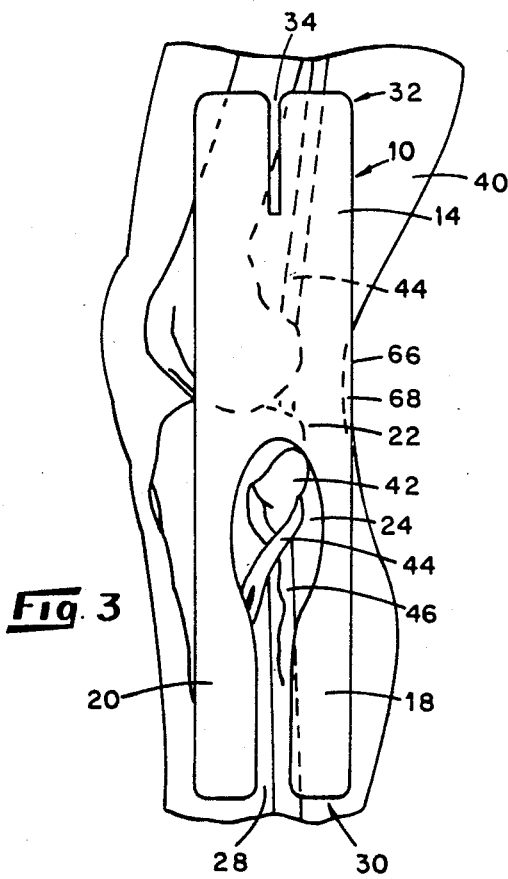
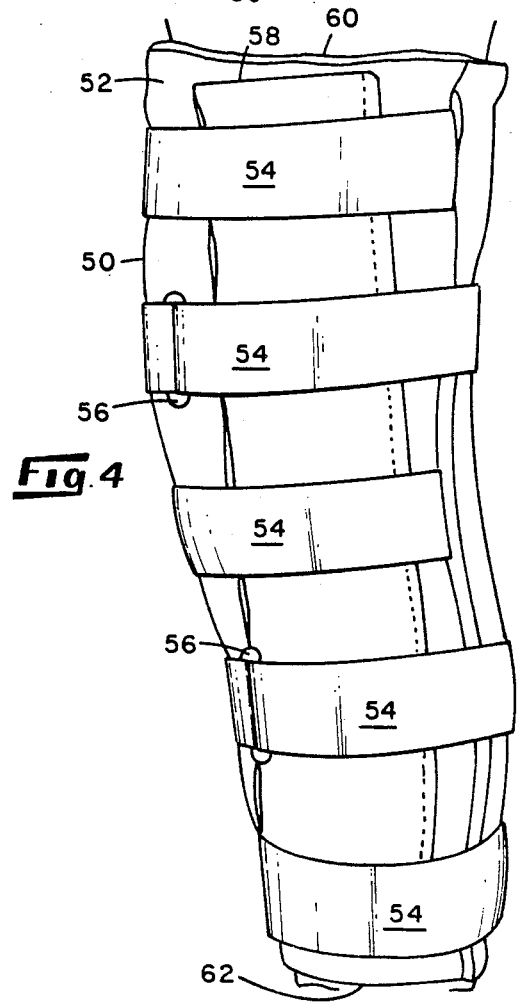
Fig. 5
Fig. 1
Fig. 2
Fig. 3
Fig. 4

STAY FOR ORTHOPEDIC APPLIANCE FOR THE KNEE

FIELD OF THE INVENTION

This invention relates to orthopedic appliances (bandages), especially such appliances intended for immobilization of the knee. In particular, it relates to stays (stiffeners) for use in such appliances.

BACKGROUND OF THE INVENTION

Following surgery on the knee it is common for the knee to be immobilized during a period of recovery. Likewise, recovery from strains or sprains is frequently enhanced by immobilization of the knee joint. In other situations, knee immobilization may be provided merely as support for weakened knees for various causes. The primary function of a knee immobilizer orthopedic appliance is to render the knee joint immobile. To appropriately perform this function, the appliance should be capable both of conforming closely to the contour of the leg above and below the knee and capable of accommodating the several protruberances associated with the knee itself. The appliance further should be capable of being relatively tightly bound about the leg in the area above the knee and below the knee and means must be provided for rigidifying the appliance to the extent that the knee joint is immobilized.

Knee movements are primarily anterior and posterior flexion of the leg about the knee joint so that the primary immobilization is directed to prevention of such flexion. Commonly, however, immobilization anticipates protection against lateral and medial flexion of the knee joint. Therefore, it is desirable in a knee immobilizer that all four flexion movements be prevented by the appliance.

Heretofore it has been common to fabricate a knee immobilizer of a relatively soft conformable body member which has one or more pockets provided at selected locations about the circumference of the appliance as it is applied to the knee and oriented along the extended leg. Stays are inserted in such pockets. These stays are referred to also at time as stabilizers or rigidifiers or stiffeners. Commonly these take the form of elongate bars that are inherently rigid, typical of these stays being aluminum or spring steel strips. Other stays have been proposed for knee immobilizer-type appliances that include ribs for enhancing the rigidity of the aluminum strips. In certain instances, it has been proposed that multiple stays be provided to insure the desired rigidity of the appliance when applied to the leg.

One of the major problems with inherently rigid stays resides in the fact that one of the most desirable locations of a stay in a knee immobilizer is directly along the medial and/or along the lateral side of the leg. A stay positioned along the lateral side of the leg places the stay directly over the peroneal nerve that originates at the lumbar fourth and fifth level and comes down around the neck of the fibula and down the lateral side of the calf. Thus, the peroneal nerve in the area of the knee is positioned between the head of the fibula and the stay of the knee immobilizer. In this position, the peroneal nerve is subject to damage as by compression or entrapment, the most frequent cause of nerve damage being compression which can result from improperly applied or ill fitting or ill designed immobilizers, etc.

Peroneal nerve damage can be temporary or permanent depending upon the circumstances of the damage. Foot drop, which is manifested by a characteristic gait, results from peroneal nerve damage. The foot flops down and slides forward because of a patient's inability to lift the foot due to the peroneal nerve damage.

It is therefore an object of the present invention to provide an orthopedic appliance particularly suitable for knee immobilization in which the appliance provides protection against peroneal nerve damage while providing the desired immobilization of the knee.

It is another object of the present invention to provide an improved stay for a knee immobilizer.

It is another object of the invention to provide a stay for a knee immobilizer wherein the stay is capable of conforming to the contour of the leg and knee and simultaneously capable of imparting the desired rigidity to the knee immobilizer.

It is another object of the present invention to provide a stay for a knee immobilizer wherein the stay provides protection for the popliteal fossa.

Other objects and advantages of the present invention will be recognized from the description contained herein, including the drawings in which:

FIG. 1 is a plan view of one embodiment of a stay in accordance with the present invention.

FIG. 2 is an elevation view of the right side of the stay depicted in FIG. 1.

FIG. 3 is a representation of a knee joint depicting the location of the peroneal nerve and the preferred location of the stay of the present invention when applied to the knee.

FIG. 4 is a representation of a knee immobilizer as applied to a patient's leg and including one embodiment of the stay of the present invention therein; and FIG. 5 is an end view of one embodiment of the stay of the present invention as bent along its longitudinal centerline when applied to the leg as in a knee immobilizer.

DETAILED DESCRIPTION OF THE INVENTION

With particular reference to FIGS. 1 and 2, one embodiment of the stay 10 of the present invention comprises a generally elongate planar member 12 having a first section 14 and a bifurcated second section indicated generally at 16 which comprises a pair of leg members 18 and 20 that preferably are integrally formed with and extend from the first section 14. In the depicted preferred embodiment the leg members 18 and 20 form a juncture indicated generally at 22 with the first section 14. At such juncture 22, there is provided a bulbous cutout 24 that defines an opening through the thickness of the stay 10 which will be recognized more fully hereinafter as being suitable for receiving therein the fibular head and that portion of the peroneal nerve that encircles the lateral side of the fibula immediately below the fibular head. This bulbous cutout preferably is located substantially centrally of the width of the stay 10 and includes a channel 26 which is a continuation of the bulbous cutout, such channel 26 extending from the juncture 22 and opening outwardly, as at 28, of the end 30 of the stay 10. Such channel 26 is generally aligned with the longitudinal centerline of the stay 10. At the opposite end 32 of the stay there is provided an elongated slot 34 which is also aligned with the longitudinal centerline of the stay and extends from a location 36 outwardly toward the end 32 of the stay. Such slot 34 functions to promote preferential bending of the first section 14 about its longitudinal centerline and preferably opens outwardly of the end 32. Whereas a closed-end slot will suffice for this function, the open-ended slot is preferred for promoting the desired bending.

In FIG. 3 there is represented one embodiment of the stay 10 of the present invention as applied in a preferred position on the lateral side of a leg 40. As depicted, the bulbous opening 24 of the stay is positioned on the leg so that the fibular head 42 is received therein. In this manner, the peroneal nerve 44 which encircles the fibular head and overlies the fibula 46 in the area immediately below the fibular head is also disposed in the bulbous opening 24. Notably, the longitudinal centerline of the stay generally is parallel to the longitudinal centerline of the leg.

In FIG. 4 there is depicted a knee immobilizer 50 comprising a generally conformable and soft body member 52 adapted to encircle the knee and a portion of the thigh and calf of the leg. One suitable body member is described in copending application Ser. No. 07/067,801 which is incorporated herein by reference. A multiplicity of straps 54 having adjustable fasteners 56 are provided to securely and releasably bind the body member 5 in encircling relationship with the leg. In the depicted body member 52 there is provided a stay pocket 58 which extends from approximately the top edge 60 of the immobilizer to the bottom edge 62 thereof. It is within this pocket 58 that the stay 10 of the present invention is positioned. Viewing FIGS. 3 and 4 provides an understanding of the positioning of the stay 10 when the knee immobilizer 50 is applied to the knee. It will be further recognized that when the body member 52 is snugly bound to the leg, the stay 10 is caused to be bent along its longitudinal centerline as it conforms to the contour of the leg. By reason of the slot 34, the bulbous cutaway 24, and channel 26, the stay preferentially bends along its longitudinal centerline and results in the first section 14 developing a ridge 53 along the longitudinal centerline thereof as best seen in FIG. 5. This ridge has been found by the inventor to act in the nature of a reinforcing rib and to impart substantial rigidity to the stay 10. This rigidity is expressed in the form of immobilization of the knee against lateral and medial flexion and against anterior and posterior flexion. It is thus possible for the stay to be manufactured with a minimum thickness which permits its ready conformability to the leg, while developing and maintaining the necessary rigidity for immobilization of the knee.

The inventor has further found that the bending of the first section 14 about its longitudinal centerline results in rotation of the leg members 18 and 20 in opposite directions about the longitudinal centerline of the stay, the leg member 18 rotating clockwise about the longitudinal centerline and the leg member 20 rotating counterclockwise about such longitudinal centerline, all as viewed in FIG. 3. The degree of rotation of the leg numbers is a function of the degree of bend of the first section 14 about its centerline. In this manner, the leg members 18 and 20 are caused to more readily conform to the contour of the calf 64 of the leg 40. When the first section 14 and the leg members 18 and 20 are secured in position by the binding forces of the body member 52, the stay assumes a rigidity, in addition to the rigidity referred to herein above by the bend in the first section 14, that precludes flexion at the knee.

In accordance with another feature of one embodiment of the present stay, a portion of the posterior edge 66 of the first section 14 of the stay, generally in the region of the juncture 22, projects posteriorly of the knee beyond the popliteal fossa 68. By this means, the stay maintains the body member 52 away from the popliteal fossa and aids in forming a pocket between the body member 52 and 10 the knee within which resides the popliteal fossa. By this means, there is prevented the exertion of excessive compression against the nerves and/or blood vessels located within the popliteal fossa, such as the popliteal artery, the popliteal vein, the tibial nerve and a portion of the peroneal nerve.

In one specific embodiment of the stay disclosed herein, the stay was fabricated from 6061 aluminum alloy. This stay was 0.040 inch thick and of uniform thickness. The first section 14 of the stay was 3 inches wide and the overall length of the stay from end 30 to end 32 was 18 inches. The bulbous cutout 24 had a lateral dimension of 1½ inches and was located generally centrally of the width of the stay. The channel 26 was a continuation of the length dimension of the bulbous cutout and extended approximately 7 inches from the bulbous cutout to open outwardly of the end 30 of the stay, thereby defining leg numbers 18 and 20 each of which was 1¼ inches wide. A slot 34 of approximately 2 inches in length and ⅛ inch width was provided opening outwardly of the end 32 of the stay.

In another embodiment of the stay, the material of construction was polyethylene compounded to provide approximately the same stiffening results as the aluminum alloy. Other conformable plastics, metals or composition materials also are suitable as materials of construction. Certain of these materials are resiliently bendable thereby making such stay useful in applications where the contour of the knee changes with time, as when swelling reduces. Less stiff flat stock can be used in multiple layers, separate or bonded, but are less desirable.

In any event, the preferred material of construction of the stay permits the stay to substantially conform to the contour of the leg, and knee to a certain extent, when the immobilizer is applied to the leg. As noted, the present stay is incorporated into a relatively soft conformable body member, for example in a pocket on the lateral side of the immobilizer. In applying the immobilizer to the leg, the bulbous cutout is located such that it surrounds the fibular head on the lateral side of the leg. The body member is then wrapped around the leg and secured snugly in place by means of the adjustable straps 54. As the straps are drawn tight, the stay is caused to bend to conform to the leg. By reason of the construction features of the present stay, it preferentially bends about its longitudinal centerline in response to the pressure applied by the straps. Such bending in the first section 14 develops the ridge 53 described hereinbefore to enhance the stiffening effect of the stay and therefor provide resistance to flexing of the knee. As the first section 14 bends, the leg members 18 and 20 are caused to rotate in different directions, one clockwise and the other counterclockwise, so that these elements also tend to conform to the leg contour. It has been found that the stiffening effect of the stay is greater when the flat stay lies snugly secured to the leg contour. In this manner, a less thick stay has been found most suitable and capable of providing the necessary stiffness without undesirable bulk. As an added benefit, flat stays are more easily contained in a pocket than rod-type and similar relatively narrow straps, or stays which include stiffening ribs or the like.

I claim:

1. In an orthopedic appliance for immobilizing a knee joint including a body member configured to at least partially encircle the leg at the knee and extending upwardly and downwardly from the knee along the thigh and calf respective distances sufficient to provide attachment locations of the body member to such thigh and calf, and covering the area of the knee within which the peroneal nerve resides, and means securing said body member to said thigh and calf, the improvement comprising an elongate stay of generally planar geometry having a width sufficient to overlie at least a majority of the lateral surface of the knee and including that lateral portion of the knee which includes a portion of the fibular head and that portion of the peroneal nerve which overlies the fibula laterally thereof and adjacent the fibular head, said stay including means defining a generally bulbous opening extending through the thickness of said stay in that portion thereof overlying said fibular head and peroneal nerve portions, said bulbous opening being of a size and geometry such that said stay does not bear substantially against such peroneal nerve portion when said stay is secured in said overlying relationship to said knee, said stay having a first generally planar section and a second bifurcated section, including first and second elongate generally planar legs disposed on opposite sides of the approximate longitudinal centerline of said stay, said stay being associated with said body member in position to overlie a lateral side of the knee and of a length sufficient to extend above and below said knee with its longitudinal centerline generally aligned with said leg when fully extended, said first section of said stay being bendable along the approximate longitudinal centerline thereof whereby said first section is caused to conform to the contour of that portion of said leg underlying said first section and said first and second leg members are caused to rotate in opposite directions and conform to the contour of said calf when said appliance is applied to the leg.

2. The improvement of claim 1 wherein said generally bulbous opening through the thickness of said stay is located generally centrally of the stay.

3. The improvement of claim 1 wherein when said appliance is applied to a knee for immobilizing said knee with the leg in a substantially fully extended position said first section includes a posterior edge portion that projects beyond the popliteal fossa of the knee to cooperatively define with said body member a protective pocket for such popliteal fossa.

4. The improvement of claim 1 and including means defining a narrow slot in that end of said first section opposite said leg members, said slot being aligned with the longitudinal centerline of said first section and opening outwardly of said opposite end of said first section.

5. The improvement of claim 1 wherein said stay is resiliently bendable.

6. The improvement of claim 1 wherein said bifurcated section includes means defining an elongated open channel extending from said bulbous opening generally along the longitudinal centerline of said stay toward one end thereof and opening outwardly of said one end and defining said first and second elongate generally planar legs.

* * * * *